United States Patent
Kühne

(10) Patent No.: US 8,251,752 B2
(45) Date of Patent: Aug. 28, 2012

(54) HIGH FREQUENCY SURGICAL DEVICE

(75) Inventor: Wolfgang Kühne, Schönfliess (DE)

(73) Assignee: Celon AG Medical Instruments (DE)

( * ) Notice: Subject to any disclaimer, the term of this patent is extended or adjusted under 35 U.S.C. 154(b) by 0 days.

(21) Appl. No.: 12/580,308

(22) Filed: Oct. 16, 2009

(65) Prior Publication Data

US 2010/0233913 A1 Sep. 16, 2010

(30) Foreign Application Priority Data

Mar. 10, 2009 (DE) .......................... 10 2009 011 912

(51) Int. Cl.
*H01R 24/04* (2006.01)

(52) U.S. Cl. ........................................ 439/668; 439/188

(58) Field of Classification Search .................. 439/668, 439/188
See application file for complete search history.

(56) References Cited

U.S. PATENT DOCUMENTS

| | | | |
|---|---|---|---|
| 4,420,216 A * | 12/1983 | Motoyama et al. | 439/188 |
| 4,936,842 A | 6/1990 | D'Amelio et al. | |
| 6,761,593 B2 * | 7/2004 | Hu | 439/668 |
| 7,361,061 B2 * | 4/2008 | Kim | 439/668 |
| 7,540,871 B2 * | 6/2009 | Gonnering | 606/34 |
| 2004/0097117 A1 | 5/2004 | Gonnering | |
| 2007/0032789 A1 | 2/2007 | Gonnering | |

FOREIGN PATENT DOCUMENTS

| | | |
|---|---|---|
| DE | 32 09 474 A1 | 9/1983 |
| GB | 2 292 264 A | 2/1996 |

OTHER PUBLICATIONS

Search Report issued by European Patent Office in connection with corresponding application No. EP 10 15 0291 on Jun. 25, 2010.

* cited by examiner

*Primary Examiner* — Truc Nguyen
(74) *Attorney, Agent, or Firm* — Ostrolenk Faber LLP

(57) ABSTRACT

The invention relates to a high frequency surgical device for generating high frequency energy for separating and/or coagulating of biological tissue, comprising at least one energy source and at least one output socket, into which a longitudinally extending electrically conductive plug contact of an electrosurgical instrument can be inserted, and which output socket comprises a catch for engaging an opposite catch configured in the plug contact, wherein a socket contact is electrically insulated from the catch, which socket contact is electrically connected to the energy source.

8 Claims, 4 Drawing Sheets

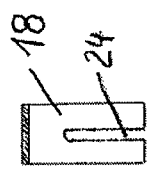
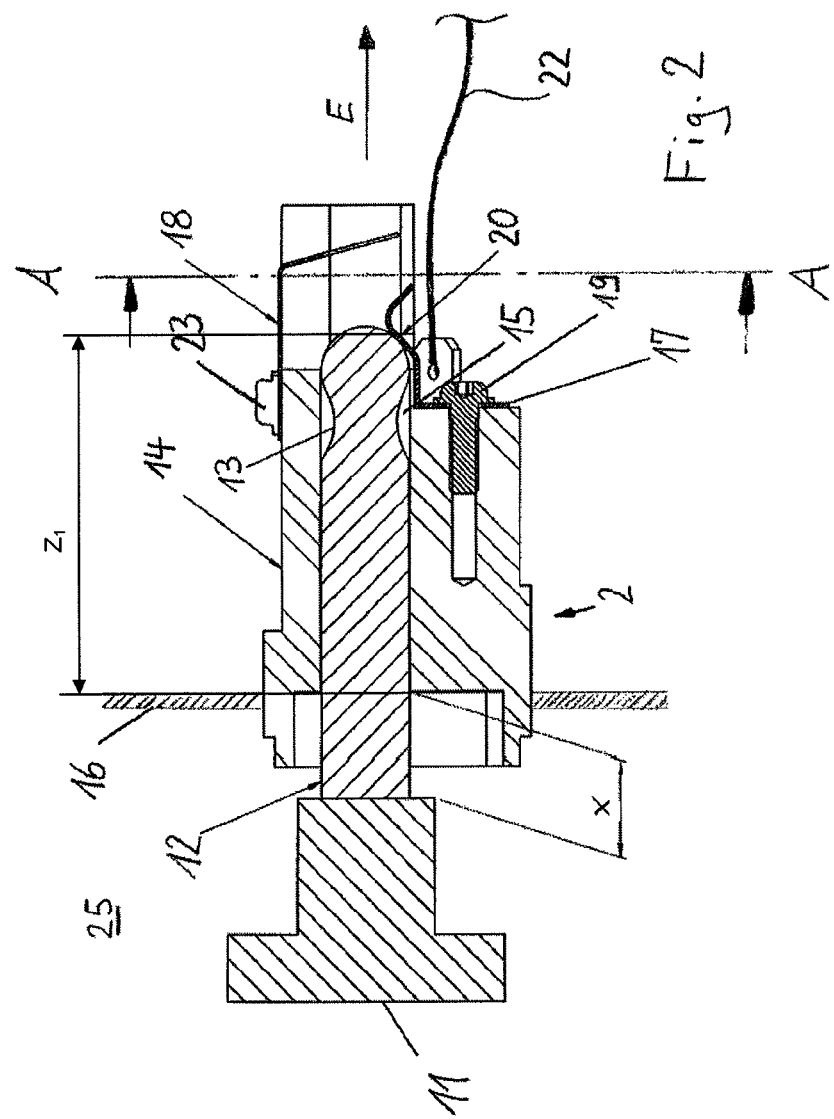

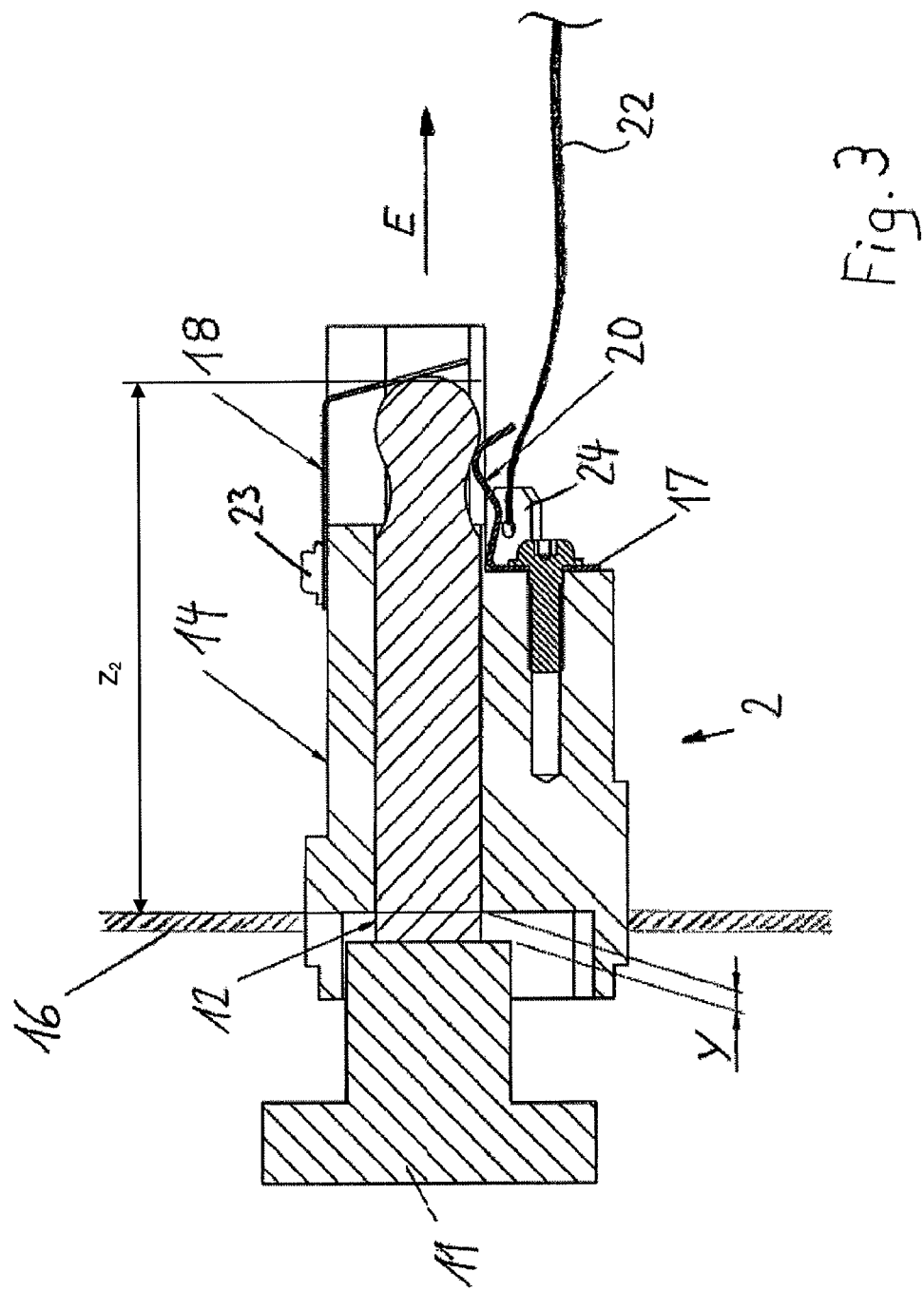

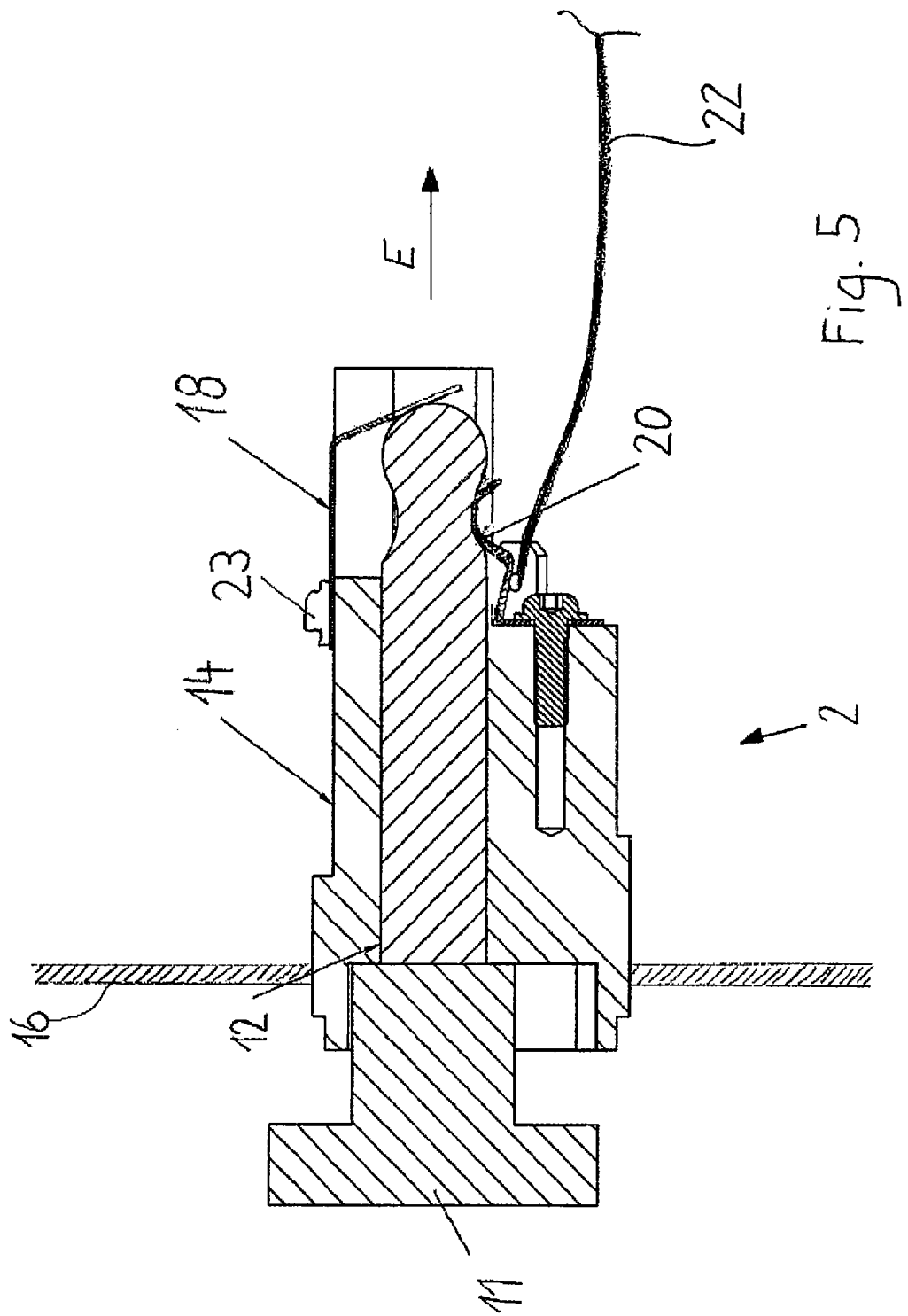

HIGH FREQUENCY SURGICAL DEVICE

BACKGROUND OF THE INVENTION

The invention relates to a high frequency surgical device for generating high frequency energy for separating and/or coagulating biological tissue with at least one energy source and with at least one output socket, into which an elongated electrically conductive plug contact of an electrosurgical instrument is insertable, and which comprises a catch for interlocking with an opposite catch configured in the plug contact.

High frequency or HF surgical devices of this type have been known for a long time in the art and they are also designated as HF generators. The HF surgical device generates HF output energy for separating or cutting and/or coagulating biological tissue. Various monopolar or bipolar instruments can be connected to the HF surgical device, which instruments induct the HF output energy into the biological tissue of a patient to be treated. The HF energy causes the desired electrosurgical separation or coagulation in the tissue or at the tissue.

In order to transmit the generated HF energy to the electrosurgical instrument, the HF surgical device often comprises one or plural output socket on its front face. Standardized plug contacts, for example, so-called Bovie plugs or Olympus 6 mm round plugs, which are part of the electrosurgical instrument, can be inserted into the output sockets. In the plugged in state, the electrically conductive plug contact is electrically connected to the energy source in the interior of the HF surgical device. Thus, the electrosurgical instrument can be loaded with HF energy during operation.

In order to fixate the plug contact in the output socket of the HF surgical device, a catch engages an opposite catch of the plug contact, when the plug contact is inserted into the output socket. In prior art devices, the catch simultaneously establishes the electrical contact between the HF surgical device and the metal plug contact.

Prior art HF surgical devices as described herein have the disadvantage that there can be an undesirable contact of a user with a plug contact that is only partially inserted, when the plug contact is already connected with the energy source of the HF surgical device. When such an undesired contact occurs, a risk for the user cannot be excluded.

SUMMARY OF THE INVENTION

It is the object of the present invention to provide a high frequency surgical device which increases the safety of the user.

This object is accomplished in the high frequency surgical device according to the invention by a socket contact which is electrically insulated from the catch, which socket contact is electrically connected to the energy source.

The solution, according to the invention, has the advantage that no energy can be transmitted to the plug contact through the catch which is electrically insulated from the energy source. The electrical connection with the energy source is only established by contacting the separate socket contact. The socket contact is disposed, so that the electrical contact with the plug contact is only established during insertion, when the insertion depth of the plug contact excludes a contact of the user.

The invention can be supplemented by various advantageous embodiments, which are described below. Thus, the maximum possible distance from a contact point with the plug contact to the outside of the high frequency surgical device can be greater for the socket contact than for the catch. This has the advantage that the electrical contact, when inserting the plug contact into the output socket, can be performed late enough and the catch can engage early in spite of that, in order to assure the fixation.

In order to implement said latest possible contacting also for plug contacts with spherical or semispherical axial ends, the socket contact can be configured so that it contacts the plug contact in plugged in state at the axial end of the plug contact.

Furthermore, the socket contact can be disposed so that it only contacts the plug contact during insertion after the catch has engaged the opposite catch substantially completely. This has the advantage that the plug contact is pulled into the contact position. Thus, a malfunction through an engaged plug contact without electrical contact can be excluded.

In order to establish a safe electrical contact between the socket contact and the plug contact, the socket contact can be made of a spring elastic material and can be configured so that it can be elastically displaced by the plug contact in inserted condition. The resulting spring force in inserted condition increases the electrical conduction. Furthermore, the catch can be made of a spring elastic material, wherein the spring constant of the catch is greater than the spring constant of the socket contact. This has the advantage that the socket contact cannot press the plug contact out of the interlock against the insertion direction.

It is advantageous to increase the contact surface with a plug contact of a single pole round plug, which plug contact is spherical or convex at its tip. Examples of such round plugs are the so-called Bovie plug or the Olympus 6 mm round plug. For this purpose, the socket plug can be configured substantially fork shaped or slotted and it can be disposed, so that the axis of the rotation symmetrical plug contact is recessed in the contact. Hereby, namely two contact portions can be implemented, which increase the electric contact surface.

The invention is described with reference to the exemplary embodiments shown in the drawing figures. The various features can be combined with each other randomly, like in the embodiments described herein.

BRIEF DESCRIPTION OF THE DRAWING(S)

FIG. 2 shows a schematic sectional view of an output socket of the high frequency surgical device according to FIG. 1 with an inserted plug contact in a first position.

FIG. 3 shows a schematic sectional view of the output socket of the high frequency surgical device according to FIG. 1 with the inserted plug contact in a second position.

FIG. 4 shows a schematic illustration of a socket contact of the high frequency surgical device according to FIG. 1 along the line A-A.

FIG. 5 shows a schematic sectional view of the output socket of the high frequency surgical device according to FIG. 1 with the inserted plug contact in a third position.

DETAILED DESCRIPTION OF THE INVENTION

Figure 1:
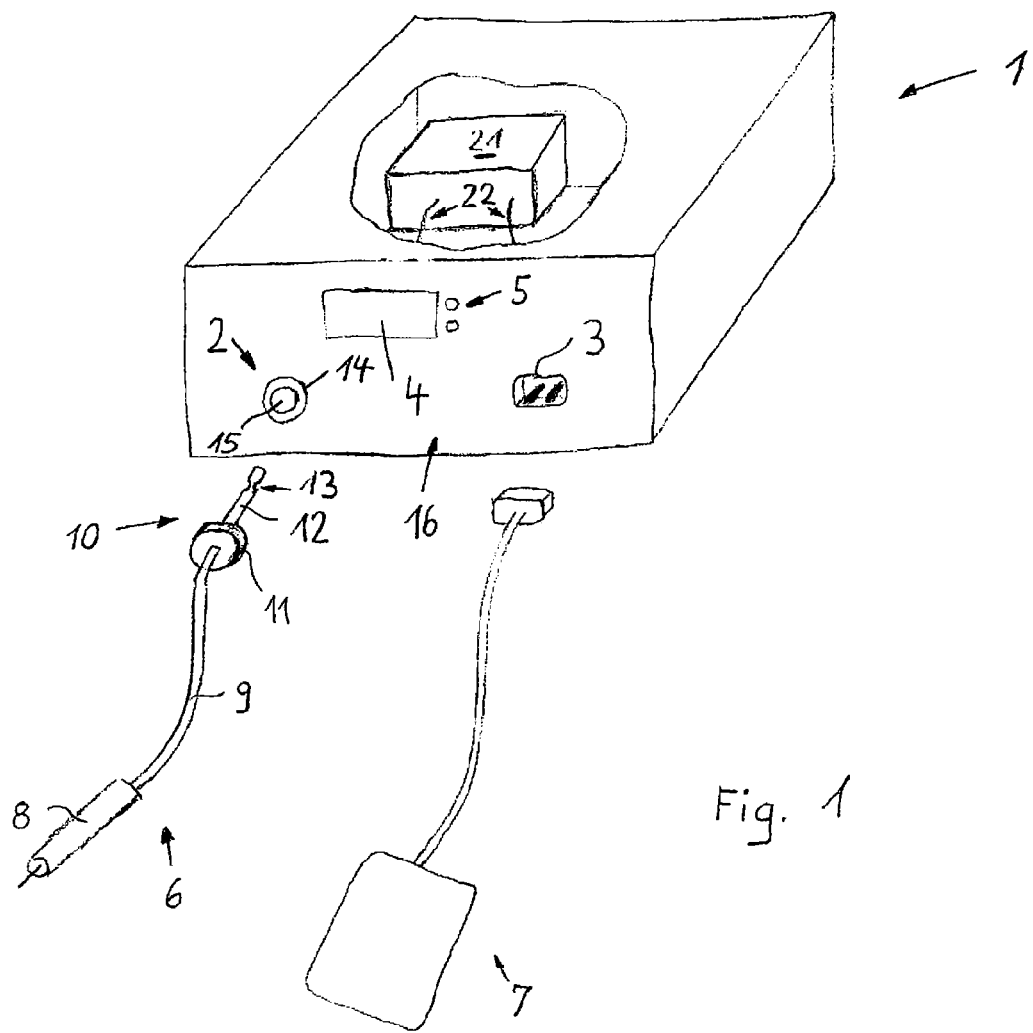
FIG. 1 shows a schematic illustration of an embodiment of a high frequency surgical device according to the invention.

Initially, the general configuration of an HF surgical device 1 according to the invention will be described with reference to the embodiment shown in FIG. 1.

The HF surgical device 1 includes an output socket 2, an input socket 3, a visualization display 4 and control elements 5 respectively disposed on the outside 25.

The HF surgical device 1 generates high frequency energy during operation for separating and/or coagulating of biological tissues. Thus, a high frequency AC voltage is provided between the output socket 2 and the input socket 3. The HF surgical device 1 includes an energy source 21 in its interior, which energy source is connected to the input socket 3 and to the output socket 2 respectively through a connection cable 22. The energy source 21 is illustrated in FIG. 1 only in a highly simplified manner. As typical in the prior art, the input socket 3 is configured as a standard socket for connecting with a connection plug of a reverse conducting electrode. The output socket 2 will be subsequently described in detail. The high frequency energy can be adjusted at the operating elements 5. Thus, the power or the operating mode can be varied. The operator obtains a visual display of some settings through the visualization display 4.

For separating and/or coagulating biological tissues, a suitable electrosurgical instrument 6 can be connected to the output socket 2 and a suitable reverse conductor electrode 7 can be connected to the input socket 3. In FIG. 1, the electrosurgical instrument 6 is, for example, an electrical scalpel for cutting tissue. Certainly, any other electrosurgical instrument can be connected.

The instrument 6 comprises a handle 8, a cable 9 and a connection plug 10. The connection plug 10, which is configured as a single pole round plug in FIG. 1, in particular as a so-called Bovie plug, comprises a housing body 11 and an electrically conductive metal plug contact 12. An opposite catch 13 is provided at the distal end of the substantially cylindrically configured plug contact 12. The opposite catch 13 is provided as a substantially concave cut in circumferential direction of the rotation symmetrical plug contact 12. The outer diameter of the plug contact 12 is approximately 8 mm in the embodiment of FIG. 1. The distal end of the plug contact 12 is configured substantially spherically.

The output socket 2 comprises an electrically non-conductive socket body 14, which is made of plastic material in the embodiment in FIGS. 1 through 5. The socket body 14 comprises a substantially cylindrical guide channel 15 in which the plug contact 12 can be received. Subsequently, the structural configuration of the output socket 2 is described, in particular, with reference to FIGS. 2 through 5.

FIGS. 2, 3 and 5 show the output socket 2 mounted to the front plate 16 of the HF surgical device 1 in a sectional view. Besides the socket contact 14 with the guide channel 15, the output socket 2 comprises a catch 17 and a socket contact 18.

The catch 17 is made of a strip of spring steel and fixated at one end at the socket body 14 with a screw 19. At the other end, the spring steel is bent into an engagement lug 20. The engagement lug 20 in the non-deflected condition, as illustrated in FIG. 2, protrudes into the guide channel 15 or into the projection of the guide channel 15 in an insertion direction E. The guide channel 15 in the socket body 14 is opened in the portion of the engagement lug 20, so that the engagement lug 20 can engage the opposite catch 13 of the plug contact 12.

The socket contact 18 is made of a strip shaped electrically well conducting piece of sheet metal, for example, copper or bronze, and mounted to the socket body 14 with a screw 23. The socket contact 18 has a contact ear 22 at one end, at which contact ear the socket contact 18 is electrically connected through the connection cable 22 to the energy source 21. At the other end, the socket contact 22 is configured with an elbow and protrudes into the guide channel 15. As shown in FIG. 4, the socket contact 18 has a straight slot 24 at this end, which slot divides the socket contact 18 and thus forms it into a fork. Similar to the catch 17, the guide channel 15 is open in the portion of the socket contact 18, so that the elbow socket contact 18 can protrude into the guide channel 15.

FIG. 2 shows the output socket 2 with the inserted plug contact 12 in a first contact position with the catch 17. In order to reach this position, the connection plug 10 is inserted into the guide channel 15 in the insertion direction E until it contacts the catch 17, but does not deflect it yet. Thus, one section of the plug contact 12 with the length x is outside of the guide channel 15. In prior art devices, the electrical connection to the energy source 21 is established in this position through the catch. Thus, the length x is large enough, so that a user can touch the plug contact 12, which is already electrically connected with the energy source, for example, with his finger. In the embodiment shown in FIG. 2, the critical length x is, for example, approximately 9 mm. In such prior art HF surgery devices, no sufficient touch protection is provided. This risk is excluded in the HF surgical device 1 according to the invention, since the catch 17 is electrically separated from the energy source 21. In the position illustrated in FIG. 2, the plug contact 12 is not connected to the energy source 21 yet.

In the HF surgery device 1 according to the invention, the electrical connection to the energy source 21 is namely only established in the first contact position illustrated in FIG. 3 through the socket contact 18. Compared to the position in FIG. 2, the plug contact 12 is inserted further into the guide channel 15 in FIG. 3. In FIG. 3, the plug contact 12 only protrudes from the guide channel 15 to the outside by a length y, wherein y is less than x, and too small for the finger of a user to touch the metal plug contact 12. For testing, a so-called standard finger can be used, which embodies the average finger of a user. In the embodiment in FIG. 3, Y is, for example, approximately 2 mm. In the position in FIG. 3, the engagement lug 20 already engages the opposite catch 13 completely, so that the connection plug 10 cannot slide out of the output socket 2 anymore. To the contrary, as soon as the engagement lug 20 engages the opposite catch 13, the spring force of the catch 17 generates a first component in the insertion direction E, which presses the plug contact 12 against the socket contact 18.

FIG. 5 shows the output socket 2 with the inserted plug contact 12 in an end position, in which the catch 17 engages the opposite catch 13 substantially completely. The engaged connection plug 10 is fixated in this position in the HF surgical device 1. The plug contact 13 elastically deflects the socket contact 18 in the insertion direction E, so that the socket contact 18 presses against the ball shaped end of the plug contact 13. This assures a good electrical contact between the socket contact 18 and the plug contact 13. In order to prevent the plug contact 18 from being pushed back out of the engagement position shown in FIG. 3, the spring constant $k_1$ of the catch 17 is greater than the spring constant $k_2$ of the socket contact 18. Therefore, the force component opposite to the insertion direction E through the socket contact 18 is smaller than the force component in the insertion direction E through the catch 17.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A high frequency surgical device configured for generating high frequency energy for separating and/or coagulating of biological tissue, the surgical device comprising:

at least one energy source;

at least one output socket of the at least one energy source, configured to receive a longitudinally extending electrically conductive plug contact of an electrosurgical instrument; and the at least one output socket comprising:

a catch positioned and configured to engage an opposite catch configured in the plug contact; and a socket contact electrically insulated from the catch and electrically connected to the energy source;

wherein the plug comprises a single contact element extending from a housing and wherein the plug and socket are configured such that the plug first contacts the catch when the plug is inserted into the socket, and wherein the plug makes electrical contact within the socket with the energy source only when the plug is sufficiently inserted within the socket such that the plug is out of accessible contact with a user of the device.

2. A high frequency surgical device according to claim 1, wherein the socket contact is disposed so that it contacts the plug contact in an inserted state at a distal end of the plug contact.

3. A high frequency surgical device according to claim 1, wherein the socket contact is disposed, so that it only contacts the plug contact during insertion after the catch has substantially completely engaged the opposite catch.

4. A high frequency surgical device according to claim 1, wherein the socket contact is made of a spring elastic material and disposed so it can be elastically displaced by the plug in contact in inserted state.

5. A high frequency surgical device according to claim 3, wherein the catch is made of a spring elastic material, wherein the spring constant of the catch is greater than the spring constant of the socket contact.

6. A high frequency surgical device according to claim 1, wherein the socket contact is substantially fork shaped or slotted.

7. A high frequency surgical device according to claim 1, wherein the output socket is configured to receive a single pole round plug, in particular a Bovie plug or an Olympus 6 mm round plug.

8. A high frequency surgical device according to claim 1, wherein the socket contact is disposed so that it contacts the plug contact in an inserted state at a distal end of the plug contact.

* * * * *